(12) United States Patent
Nagao et al.

(10) Patent No.: US 7,951,277 B2
(45) Date of Patent: May 31, 2011

(54) GAS SENSOR AND METHOD FOR MANUFACTURING THE SAME

(75) Inventors: Yukinobu Nagao, Aichi (JP); Masaki Nakagawa, Aichi (JP); Takeshi Kawai, Aichi (JP); Ryohei Aoki, Aichi (JP); Satoshi Teramoto, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1046 days.

(21) Appl. No.: 11/349,177

(22) Filed: Feb. 8, 2006

(65) Prior Publication Data
US 2006/0185978 A1 Aug. 24, 2006

(30) Foreign Application Priority Data
Feb. 8, 2005 (JP) ................. 2005-032241

(51) Int. Cl.
*G01N 27/407* (2006.01)
(52) U.S. Cl. ........................ 204/426; 204/424
(58) Field of Classification Search .................. 204/426, 204/424
See application file for complete search history.

(56) References Cited

U.S. PATENT DOCUMENTS

| | | | |
|---|---|---|---|
| 4,956,072 A | | 9/1990 | Kojima et al. |
| 5,171,335 A | * | 12/1992 | Kojima et al. ............. 55/523 |
| 5,419,828 A | * | 5/1995 | Nakano et al. ............. 204/425 |
| 5,985,118 A | * | 11/1999 | Makino et al. ............. 204/426 |
| 2003/0159928 A1 | * | 8/2003 | Kojima et al. ............. 204/408 |
| 2004/0084309 A1 | * | 5/2004 | Ando et al. ............. 204/426 |
| 2004/0154920 A1 | * | 8/2004 | Schneider et al. ............. 204/431 |

FOREIGN PATENT DOCUMENTS

| | | |
|---|---|---|
| JP | 60113550 U | 8/1985 |
| JP | 1-140055 | 6/1989 |
| JP | 1219662 A | 9/1989 |
| JP | 2612584 | 2/1997 |
| JP | 2001242122 A * | 9/2001 |
| JP | 2003-322632 | 11/2003 |
| JP | 2004239688 A | 8/2004 |

OTHER PUBLICATIONS

English Abstract of JP 2001-242122.*
Japanese Office Action dated Dec. 7, 2010 issued in corresponding to Japanese Patent Application No. 2006-030533.

* cited by examiner

*Primary Examiner* — Harry D Wilkins, III
*Assistant Examiner* — Bryan D. Ripa
(74) *Attorney, Agent, or Firm* — Sughrue Mion, PLLC

(57) ABSTRACT

A prismatic multilayer gas sensor element and method of making the same, the prismatic multilayer gas sensor element (1) having a substantially rectangular cross section, and including a gas-sensing cell portion (2) formed at a distal end portion of the prismatic gas sensor element (1); and a posterior lead portion (3) adjoining the gas-sensing cell portion (2). The longitudinal lateral surfaces of the posterior lead portion (3) are coated with a non-porous alumina layer (11), the non-porous alumina layer (11) having a multilayered structure including at least a joining layer (11a) and a surface layer (11b). The longitudinal lateral surface of the gas-sensing portion (2) is not coated with a non-porous alumina layer.

12 Claims, 9 Drawing Sheets

GAS SENSOR AND METHOD FOR MANUFACTURING THE SAME

BACKGROUND OF THE INVENTION

1. The Field of the Invention

The present invention relates to a gas sensor, such as an oxygen sensor, an A/F (air/fuel ratio) sensor, a NOx sensor, or a HC sensor for use, for example, in controlling exhaust gas from an internal combustion engine of an automobile. More particularly, the invention relates to a prismatic multilayer ceramic gas sensor element having a substantially rectangular cross section and comprising a zirconia solid electrolyte layer and an alumina layer. The invention further relates to a method of manufacturing the gas sensor.

2. Description of the Related Art

Japanese Patent 1219 662 discloses an oxygen detection element having a rectangular cross section, comprising a laminate of a solid electrolyte plate of $ZrO_2$, electrodes, an electrode lead formed on the solid electrolyte plate, a protection layer coated on the solid electrolyte layer and the lead, and a U-shaped frame body. The lateral surfaces of the laminate are covered with a gas-impermeable layer of alumina so as to maintain insulation resistance between the electrode and a metallic housing body even if a conductive material accumulates thereon.

United States Patent Application Publication US 2003/0159928A1 discloses a prismatic multilayer ceramic gas sensor element having a rectangular cross section, comprising a solid electrolyte layer co-fired with a ceramic heater substrate. A porous alumina layer is coated around a gas sensing cell portion formed at a distal end of the prismatic multilayered gas sensor element so as to prevent the gas sensor element from cracking induced by contact with water droplets.

3. Problems to be Solved by the Invention

The present inventors have found that carbon or soot exhausted from an internal combustion engine, and accumulating on the lateral surface of a prismatic multilayer ceramic gas sensor element, may cause "blackening" or deoxidization of the solid electrolyte layer laminated in a posterior lead portion adjoining a gas sensing cell portion of the gas sensor element.

The deoxidized solid electrolyte layer may cause serious problems, including reduced insulation resistance between the metallic lead connected to a gas sensing cell electrode formed at a distal end portion of the prismatic multilayer gas sensor element and a metallic housing supporting the gas sensor element at its posterior lead portion adjoining the gas sensing cell portion, a malfunctioning gas sensing mechanism, and weakened mechanical strength due to brittleness of the deoxidized solid electrolyte layer.

Conventionally, a prismatic multilayer gas sensor element has been made by cutting a sheet-like laminate comprised of an oxygen-ion conductive solid electrolyte layer and insulating ceramic layers sandwiching the solid electrolyte layer, and coating cut-surfaces (corresponding to the lateral surfaces of the prismatic multilayer ceramic gas sensor element) with an insulating protective layer so as to prevent the oxygen ion conductive solid electrolyte layer from being directly exposed to an ambient gas atmosphere.

An analysis conducted by the present inventors indicated that this "blackening" or deoxidization of the solid electrolyte layer starts to occur particularly at the cut-surfaces corresponding to the lateral surfaces of the posterior lead portion adjoining the gas sensing portion. In this regard, carbon-like soot accumulates on the protective layer formed on the lateral surfaces when an electrical voltage is applied across the leads sandwiching the solid electrolyte layer and a metallic housing supporting the posterior lead portion of the prismatic gas sensor.

Notably, the deoxidization of the zirconia solid electrolyte layer does not occur at the gas sensing cell portion of the prismatic multilayer gas sensor, while it may occur at the posterior lead portion adjoining the gas sensing cell portion. The reason for this is considered to be as follows. Since the posterior lead portion in which a zirconia solid electrolyte layer is sandwiched by metallic leads running from the gas sensing cell electrodes formed at a distal end portion of the prismatic sensor element to a rear end potion thereof is supported by a housing member for holding the gas sensor element, the temperature of the posterior lead portion can not be elevated to burn off carbon-like soot accumulating thereon. On the other hand, the gas sensing cell portion is heated to a temperature that is high enough to burn off the carbon-like soot.

Therefore, there is a need for an improved protective insulating layer for coating on the lateral surfaces of the lead portion of a prismatic gas sensor in view of resistance against carbon or soot-fouling, as well as an improved thermo-positional relationship between the gas sensing cell portion and the posterior lead portion in view of effective thermal oxidation or burning off of carbon-like soot accumulating on the prismatic multilayer ceramic gas sensor element.

SUMMARY OF THE INVENTION

The present invention has been achieved so as to solve the above-mentioned problems relating to soot fouling or deoxidization of the zirconia solid electrolyte layer constituting a prismatic multilayer ceramic gas sensor element, caused by carbon or carbon-like soot accumulating on the protective insulating layer formed on cut-surfaces or lateral surfaces of a posterior lead portion adjoining a gas sensing portion of the gas sensor element.

It is therefore an object of the invention to provide an improved prismatic multilayer gas sensor element comprising a zirconia solid electrolyte layer and a protective insulating layer, particularly an improved protective insulating layer formed on lateral surfaces of a posterior lead portion adjoining a gas sensing cell of the prismatic multilayer gas sensor, and having an improved thermo-positional relationship between the gas sensing cell portion and the posterior lead portion against carbon soot-fouling or deoxidization of the zirconia solid electrolyte layer.

A second object of the invention is to provide a method of manufacturing an improved prismatic multilayer gas sensor element having improved resistance against soot fouling or deoxidization of the zirconia solid electrolyte layer.

The above first object of the invention is achieved by providing a prismatic multilayer gas sensor element (1) having a substantially rectangular cross section, comprising:

a gas-sensing cell portion (2) formed at a distal end portion of the prismatic gas sensor element (1), comprising a zirconia solid electrolyte layer (4) and a gas-detecting electrode (5) and a reference electrode (6) formed on top and bottom planer surfaces of the zirconia solid electrolyte layer (4), respectively;

a posterior lead portion (3) adjoining the gas-sensing cell portion (2) and extending to a rear end portion of the prismatic gas sensor element (1), comprising the zirconia solid electrolyte layer (4) longitudinally extending from the gas sensing portion (2), a first metallic lead (5a) and a second metallic lead (6a) connected to the gas-detecting electrode (5) and the reference electrode (6), respectively, the first and second metallic leads being formed on the top and bottom planer surfaces of the solid electrolyte layer (4) and extending from the posterior lead portion (3), respectively, a first non-porous alumina layer (8) covering the top planer surface of the zirconia solid electrolyte layer (4) and the first metallic lead (5a) formed thereon, and a second non-porous alumina layer (7) covering the bottom planer surface of the zirconia solid electrolyte layer (4) and the second metallic lead (6a) formed thereon;

and a heating resistor (12a) sandwiched by insulating layers (7, 10) and positioned in the vicinity of the gas-sensing portion (2) so as to heat the gas-sensing portion (2) to a temperature of more than 600° C.;

wherein longitudinal lateral surfaces of the posterior lead portion (3), which lateral surfaces are substantially perpendicular to top and bottom planer surfaces of the prismatic multilayer gas sensor element (1), and which lateral surfaces are heated by the heating resistor (12a) to a temperature not exceeding 600° C., are each coated with a third non-porous alumina layer (11).

An important feature of the above prismatic multilayer gas sensor element according to the invention is that the third and fourth non-porous alumina layers are coated on the longitudinal lateral surfaces (or cut surfaces) of the posterior lead portion adjoining the gas sensing cell formed at a distal end portion of the prismatic multilayer gas sensor element, but lateral surfaces of the gas sensing portion are not coated with the non-porous alumina layers.

Preferably, the non-porous alumina coating layer formed on the lateral surface of the lead portion adjoining the gas sensing cell portion assumes a multilayer structure including at least a joining layer and a surface layer. Herein, the expression "non-porous" means that pores of the alumina coating layer are small enough to prevent particles of carbon-like soot from passing through the alumina coating layer and reaching an underlying solid electrolyte layer. The multilayer structure of the alumina coating layer formed on the lateral surface of the lead portion more effectively prevents intrusion of particles of carbon-like soot, compared to a single alumina coating layer formed on the lateral surface, according to the invention.

When the multilayer structure of the alumina coating layer formed on the lateral surface of the posterior lead portion of the prismatic multilayer gas sensor element is rendered "non-porous" or impermeable against carbon-like soot to thereby protect the zirconia solid electrolyte layer from the carbon-like soot, a total fired thickness of the non-porous alumina layer including the joining surface and the surface layer can be advantageously made as thin as about 2-30 µm, each layer having a fired thickness of about 2-25 µm, according to an aspect of the invention.

A single layer alumina coating of the same thickness of 2-30 µm as formed on the lateral surface of the solid electrolyte layer is apt to be "porous" and cannot fully prevent carbon particles from reaching the zirconia solid electrolyte layer through the single alumina layer formed on the cut surface of the prismatic multilayer gas sensor. A conventional single layer alumina coating formed on the lateral side the prismatic gas sensor is typically more than 30 µm thick.

One reason that a multilayer alumina coating layer structure coated on the lateral surface of the prismatic multilayer gas sensor element is advantageous is that a high laminating pressure can not be applied to the cut surface of unfired multilayer prismatic gas sensor element during an alumina coating process so as to eliminate pores or micro air bubbles from an unfired alumina coating layer formed on the cut surface, whereas sufficient pressure can be readily applied so as to eliminate pores or micro air bubbles during a sheet laminating process in which an unfired zirconia solid electrolyte sheet and unfired alumina sheets are laminated. In other words, a multilayer structured alumina coating layer including at least a joining layer and a surface layer reduces porosity of the alumina coating layer so as to make it "non-porous" against carbon intrusion, even if thin.

The posterior lead portion of the prismatic multilayer gas sensor element according to the invention preferably comprises a zirconia solid electrolyte layer; and first and second metallic leads sandwiching the zirconia solid electrolyte layer and respectively connecting to a metallic measuring electrode and a reference electrode to constitute a gas sensing cell formed at a distal end portion of the prismatic gas sensor element; first and second non-porous alumina coating layers formed respectively on bottom and top surfaces of the zirconia solid electrolyte layer; and a third non-porous alumina layer coated on at least longitudinal lateral surfaces of the zirconia solid electrolyte layer; wherein the third non-porous alumina layer has a multilayer structure including a joining layer attached to the lateral surface of the zirconia solid electrolyte layer and a surface layer covering the joining layer.

A gas sensing cell portion formed at a distal end of the prismatic gas sensor element and adjoining the posterior lead portion comprises a zirconia solid electrolyte layer extending from the posterior lead portion; and metallic cell electrodes sandwiching the zirconia solid electrolyte layer, the metallic cell electrodes connecting to the leads in the posterior lead portion and running in a longitudinal direction of the prismatic gas sensor element.

In the prismatic multilayer gas sensor element according to the invention, the zirconia solid electrolyte layer laminated in the posterior portion adjoining the gas sensing portion is not heated by a heating resistor of a ceramic heater positioned in the vicinity of the gas sensing cell to a temperature that is high enough to burn off carbon-like soot accumulation. On the other hand, the zirconia solid electrolyte layer constituting a gas sensing cell formed at a distal end portion of the prismatic sensor element is designed to be exposed to an ambient gas atmosphere through a porous material such as a porous alumina layer formed close to or on the zirconia solid electrolyte layer, and to be heated to a high temperature of more than 600° C. so as to burn off carbon-like soot by means of the ceramic heater positioned close to the gas sensing cell.

In order to prevent the zirconia solid electrolyte layer from becoming deoxidized or "blackened" by carbon-like soot accumulating on the posterior lead portion which is not elevated to a temperature of higher than 600° C., non-porous alumina layers are formed on the cut surfaces of the zirconia solid electrolyte layer constituting the posterior portion, according to the invention. On the other hand, since the zirconia solid electrolyte layer constituting the gas sensing cell portion is heated to a temperature of higher than 600° C. by a heater positioned close thereto, cut surfaces of the zirconia solid electrolyte layer constituting the gas sensing cell portion can be directly exposed to exhaust gas containing carbon-like soot.

An advantage of the prismatic multilayer gas sensor element according to the invention is that because non-porous alumina layer having a multilayer structure is coated on cut surfaces (corresponding to lateral surfaces formed perpendicular to top and bottom surfaces) of the posterior lead portion of the prismatic multilayer gas sensor, including a lateral surface (i.e., a cut surface) of the solid electrolyte layer, carbon-like soot exhausted from an internal combustion engine does not accumulate on the cut surface and does not deoxidize the zirconia solid electrolyte layer. Deoxidization by the carbon-like soot of the zirconia solid electrolyte layer is thus prevented. As a result, accurate measurement of a gas such as oxygen concentration during a gas sensing operation can be advantageously secured for a long period of time.

Preferably, the non-porous alumina layer having a multilayer structure formed on the lateral surface of the zirconia solid electrolyte layer constituting the posterior portion of the prismatic gas sensor element has a total fired thickness of 2-30 μm, more preferably, 5-25 μm, most preferably 10-20 μm, including the thickness of a joining layer and the thickness of a surface layer of the multilayer structure. If the total fired thickness is less than 2 μm, a desired insulation resistance of at least 1 M ohm between the lead embedded in the prismatic gas sensor and the metal housing supporting the prismatic gas sensor can not be maintained when carbon-like soot accumulates on the non-porous alumina layer during a gas detecting operation of exhaust gas exhausted from an internal combustion engine. If the total fired thickness of the non-porous alumina layer is too thick, e.g., 100 μm, the thermal expansion difference between the zirconia solid electrolyte layer and the non-porous alumina coating layer coated thereon may cause cracking of the zirconia solid electrolyte layer constituting the prismatic multilayer gas sensor element during the gas detecting operation.

The non-porous alumina layer coated on the lateral surface of the posterior lead portion of the prismatic multilayer gas sensor element is formed by co-firing the unfired prismatic multilayer gas sensor element and the unfired alumina coating layer coated thereon at a temperature of about 1350-1550° C. The non-porous alumina layer may comprises 90-99.9% percent by weight of $Al_2O_3$ and 0.01-10% by weight of inorganic binders such as MgO, $SiO_2$ and CaO. A more preferable range for the $Al_2O_3$ content is 99% to 99.9% by weight.

The gas sensing cell portion formed at a distal end portion of the prismatic multilayer gas sensor, which is exposed to an ambient atmosphere, is preferably located at a distance of about 0.5-6.5 mm from the distal end of the prismatic gas sensor. In this manner, the heater positioned close to the gas sensing cell portion can quickly heat the gas-sensing portion to a temperature of at least 600° C. to burn off carbon-like soot if deposited thereon.

The posterior lead portion adjoining the gas sensing cell portion, which requires a non-porous alumina layer coated thereon since its temperature is not elevated to exceed 600° C., is therefore located at a distance of about 6.5 mm away from the distal end of the prismatic multilayer gas sensor to a rear end portion thereof. The temperature of the posterior lead portion is kept comparatively low, and most of the posterior portion except its portion adjoining the gas sensing portion is not elevated to exceed 600° C. during the gas detecting operation. Carbon-like soot accumulates on such a comparatively low-temperature portion of the posterior lead potion, which is exposed to the exhaust gas atmosphere.

Normally, the zirconia solid electrolyte layer constituting the gas sensing portion formed at the distal end portion of the prismatic multilayer gas sensor element is not soot-fouled or deoxidized. This is because a heater provided close to the gas-sensing cell is designed to elevate the temperature of the gas sensing cell portion to a temperature that is high enough to burn off carbon-like soot if deposited on the gas sensing cell portion. Notably, the carbon-like soot is not burnt off if the temperature of the gas sensing portion or the posterior lead potion is below 600° C.

The longitudinal lateral surfaces of the posterior lead portion including the lateral surface of the zirconia solid electrolyte layer(s), which are not heated to a temperature of 600° C. or higher, are coated with the non-porous alumina layer, according to the invention.

The second object of the invention is achieved by providing a method of manufacturing a multilayer prismatic gas sensor having a substantially rectangular cross section, which comprises:

forming a plurality of unfired metallic electrodes on a top surface of a green zirconia solid electrolyte sheet;

forming a plurality of unfired metallic reference electrodes on the bottom surface of the green solid electrolyte sheet (so that a plurality of gas sensing cells are formed);

forming a plurality of unfired first and second metallic leads on the bottom and top surfaces of the green solid electrolyte layer, respectively, the first metallic leads connecting to respective reference electrodes and the second metallic electrodes connected to respective measuring electrodes to form a plurality of posterior lead portions each adjoined to a gas sensing portion;

forming an unfired laminate sheet by laminating a first green alumina sheet on the bottom surface of the green solid electrolyte layer and the first metallic leads and laminating a second green alumina sheet on the top surface of the green solid electrolyte layer and the second metallic leads;

cutting the unfired laminate sheet into a plurality of unfired prismatic multilayer gas sensor elements;

forming on cut-surfaces of the posterior lead portions constituting unfired prismatic gas sensor elements, a first paste layer comprising alumina particles and a solvent and then drying the first paste layer to form a joining layer;

forming on the first dried paste layer, a second paste layer comprising alumina particles and a solvent and then drying the second paste layer to form a surface layer; and firing the unfired prismatic multilayer gas sensor elements at a temperature of 1350-1550° C. so as to obtain a plurality of fired prismatic gas sensor elements.

In the above method, the unfired first and second paste layers each are preferably about 3-20 μm thick, so that a total thickness of the non-porous alumina layer including a joining layer and a surface layer after firing becomes about 2-30 μm.

The present invention can be applied not only to a prismatic multilayer gas sensor element comprising a single solid electrolyte layer sandwiched by alumina layers, but also to a prismatic multilayer gas sensor element comprising two or more solid electrolyte layers each sandwiched by alumina layers and/or comprising a ceramic heater substrate laminated on the prismatic gas sensor, so long as the solid electrolyte layer constituting the posterior lead potion adjoining the gas sensing portion of the prismatic multilayer gas sensor has cut-surfaces perpendicular to top and bottom surfaces of the prismatic multilayer gas sensor element, and the temperature of the cut-surfaces is less than 600° C. during a gas detecting operation of the prismatic gas sensor placed in exhaust gas exhausted from an internal combustion engine.

Since a higher voltage is usually applied across metallic leads of the electrodes of a pumping cell constituting a multi-cell type prismatic gas sensor element comprising plural solid electrolyte layers (referring to FIG. 5 discussed below) than across metallic leads of the electrodes of an EMF cell (electromotive force cell) constituting a single-cell type prismatic gas sensor element using a single solid electrolyte layer (referring to FIG. 1 discussed below), a more prominent effect of the present invention will be apparent in a multi cell type prismatic gas sensor element having a non-porous alumina layer formed on the longitudinal lateral surface thereof.

DETAILED DESCRIPTION OF THE INVENTION

The present invention will next be described in further detail. However, the present invention should not be construed as being limited thereto.

The present invention provides a prismatic gas sensor element having a multilayered structure, including a ceramic heater laminated thereon, for use in a gas sensor comprising a sensor housing.

Figure 1:
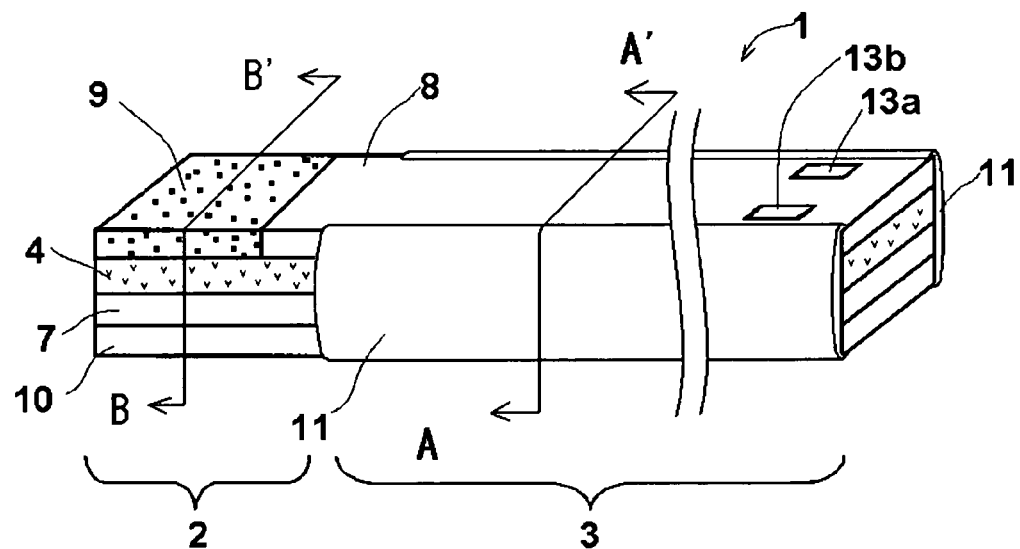
FIG. 1 is a perspective view showing a prismatic multilayer gas sensor element according to the present invention.
Figure 5:
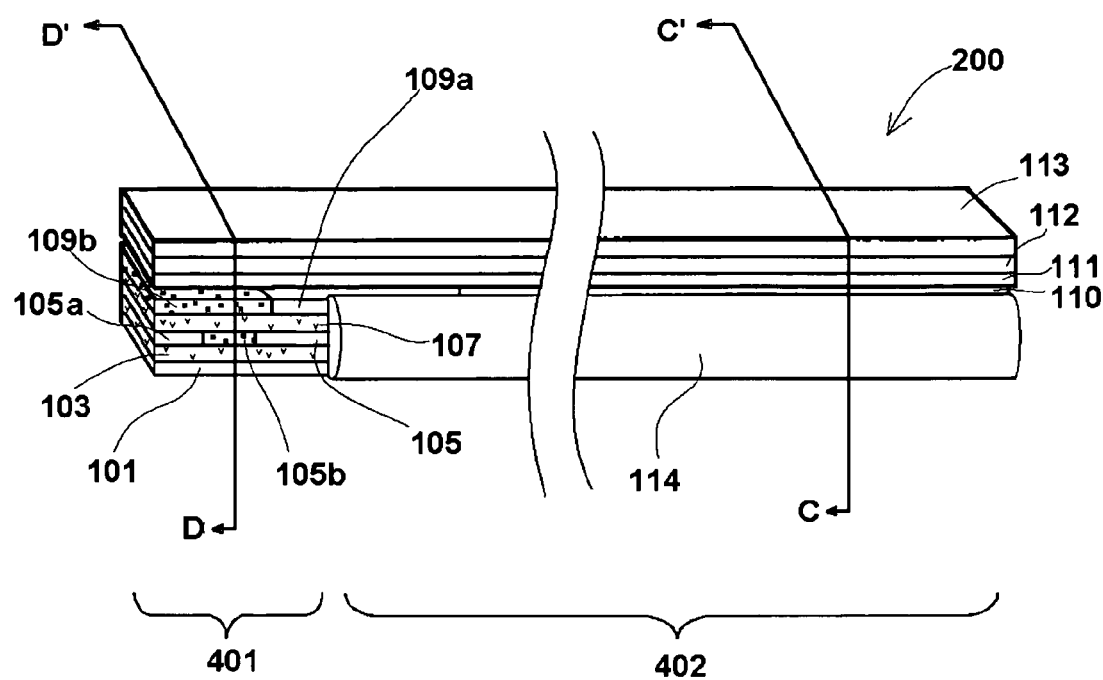
FIG. 5 is a perspective view showing another prismatic multilayer gas sensor element according to the present invention.
Figure 6:
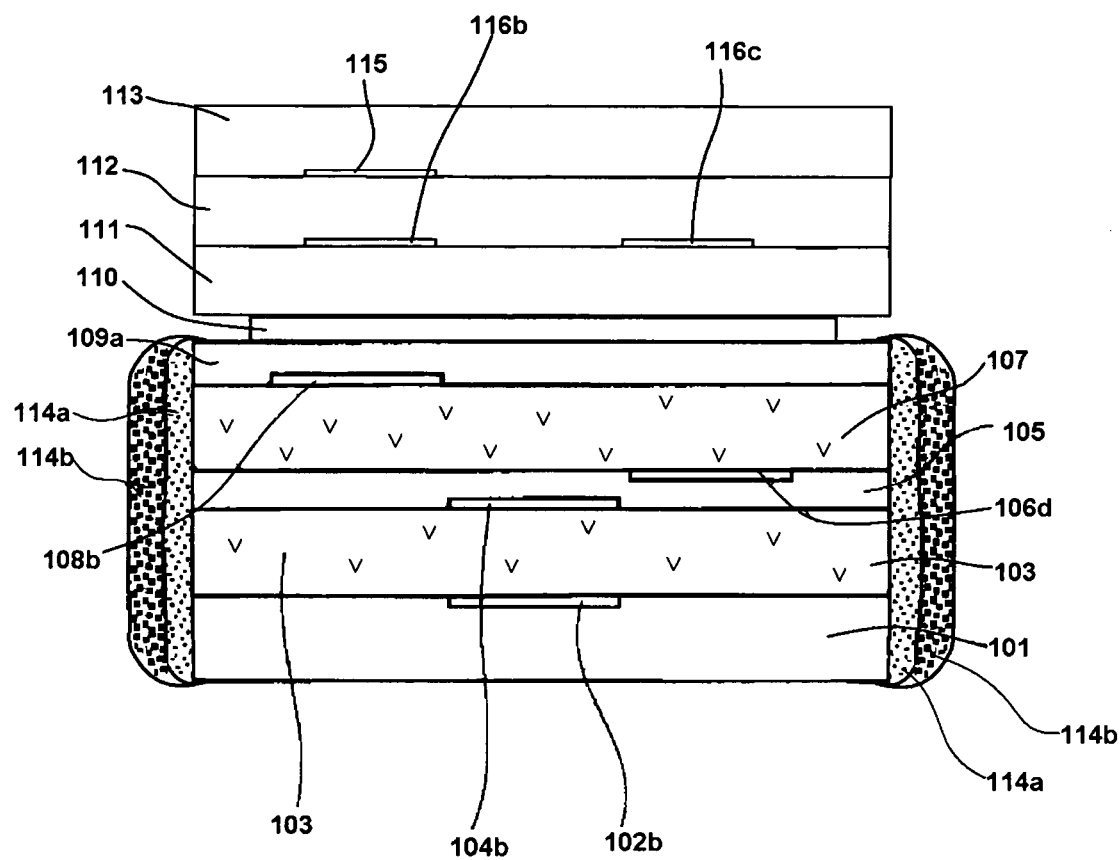
FIG. 6 is a schematic cross-sectional view, as cut along line C-C' line of FIG. 5, showing the internal structure of a posterior lead portion of the prismatic multilayer gas sensor element of FIG. 5.

A shown in FIG. 1 or FIG. 5, the prismatic multilayer gas sensor element (1, 200) according to the invention, comprises a gas-detecting cell portion or rather gas-sensing cell portion (2, 401) formed at a distal end portion thereof; and a posterior lead portion (3, 402) adjoining the gas sensing portion (2, 401) which extends longitudinally from a distal end to a rear end of the prismatic gas sensor element (1, 200). A ceramic heater comprising alumina ceramic layers (7, 10), (111, 112) and a heating resistor (12a, 116a—see FIGS. 3 and 7) is laminated on the prismatic gas sensor (1, 200) so as to heat the gas-sensing portion (2, 401).

The prismatic multilayer gas sensor element 1 shown in FIG. 1 comprises an oxygen-ion conductive solid electrolyte layer 4 made of stabilized or partially stabilized zirconia ceramic, which extends longitudinally from a distal end to a rear end of the prismatic gas sensor element 1. The prismatic gas sensor element 1 further comprises non-porous insulating layers (7, 8) comprised of alumina ceramic, which sandwich the solid electrolyte layer 4. A porous alumina layer 9 is coated on the solid electrolyte layer 4 only at the gas-sensing cell portion 2 so that exhaust gas, including various gases, exhausted from an internal gas combustion engine can reach to the solid electrolyte layer 4 forming the gas sensing cell.

Figure 2:
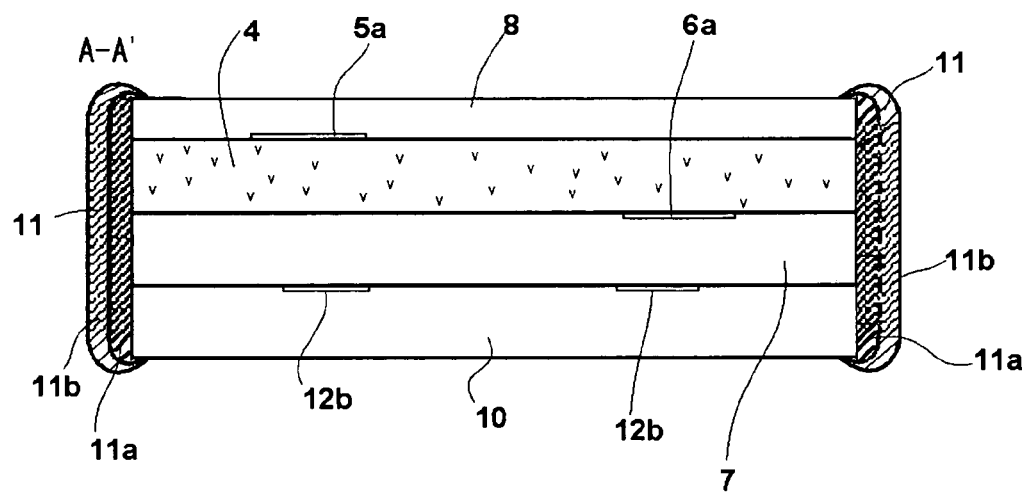
FIG. 2 is a schematic cross-sectional view, as cut along line A-A' line of FIG. 1, showing the internal structure of a posterior lead portion of the prismatic multilayer gas sensor element of FIG. 1.
Figure 3:
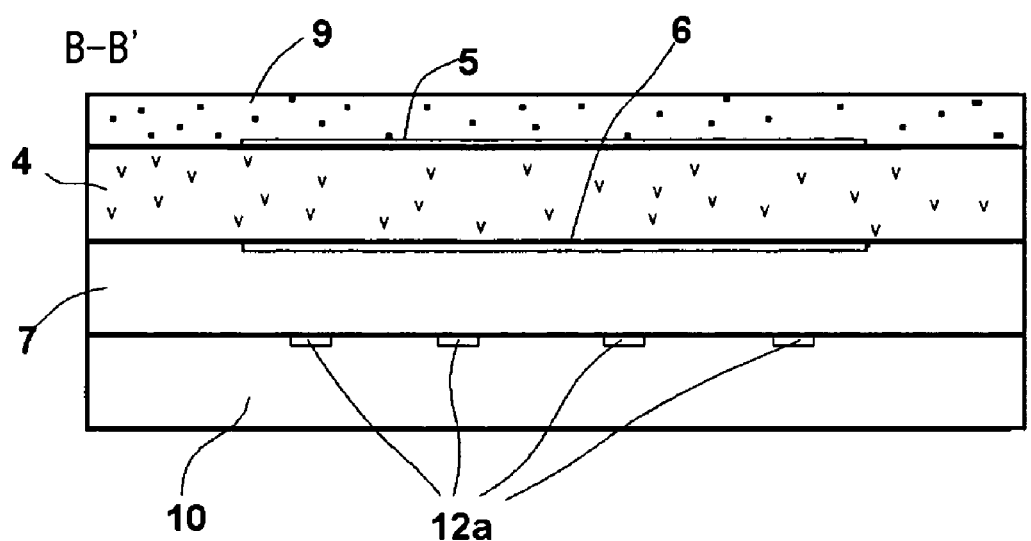
FIG. 3 is a schematic cross-sectional view, as cut along line B-B' line of FIG. 1, showing the internal structure of a gas-sensing portion of the prismatic multilayer gas sensor element of FIG. 1.

FIG. 2 is a schematic cross-sectional view of the posterior lead portion 3 adjoining the gas sensing portion 2, as cross-sectioned along line A-A' of FIG. 1, showing the internal structure of the posterior lead potion 3 of the prismatic gas senor 1 of FIG. 1. As shown in FIG. 2, a first metallic lead (5a) and a second metallic lead (6a) (respectively connecting to gas-detecting electrode 5 and reference electrode 6 as shown in FIG. 3) are formed respectively on the top and bottom planer surfaces of the solid electrolyte layer 4 extending from the posterior lead portion 3. A first non-porous alumina layer 8 is laminated on a top planer surface of the zirconia solid electrolyte layer 4 so as to cover the top surface thereof and the first metallic lead (5a) formed thereon. A second non-porous alumina layer 7 is laminated on a bottom planer surface of the zirconia solid electrolyte layer 4 so as to cover the bottom surface thereof and the second metallic lead (6a) formed thereon.

Figure 4:
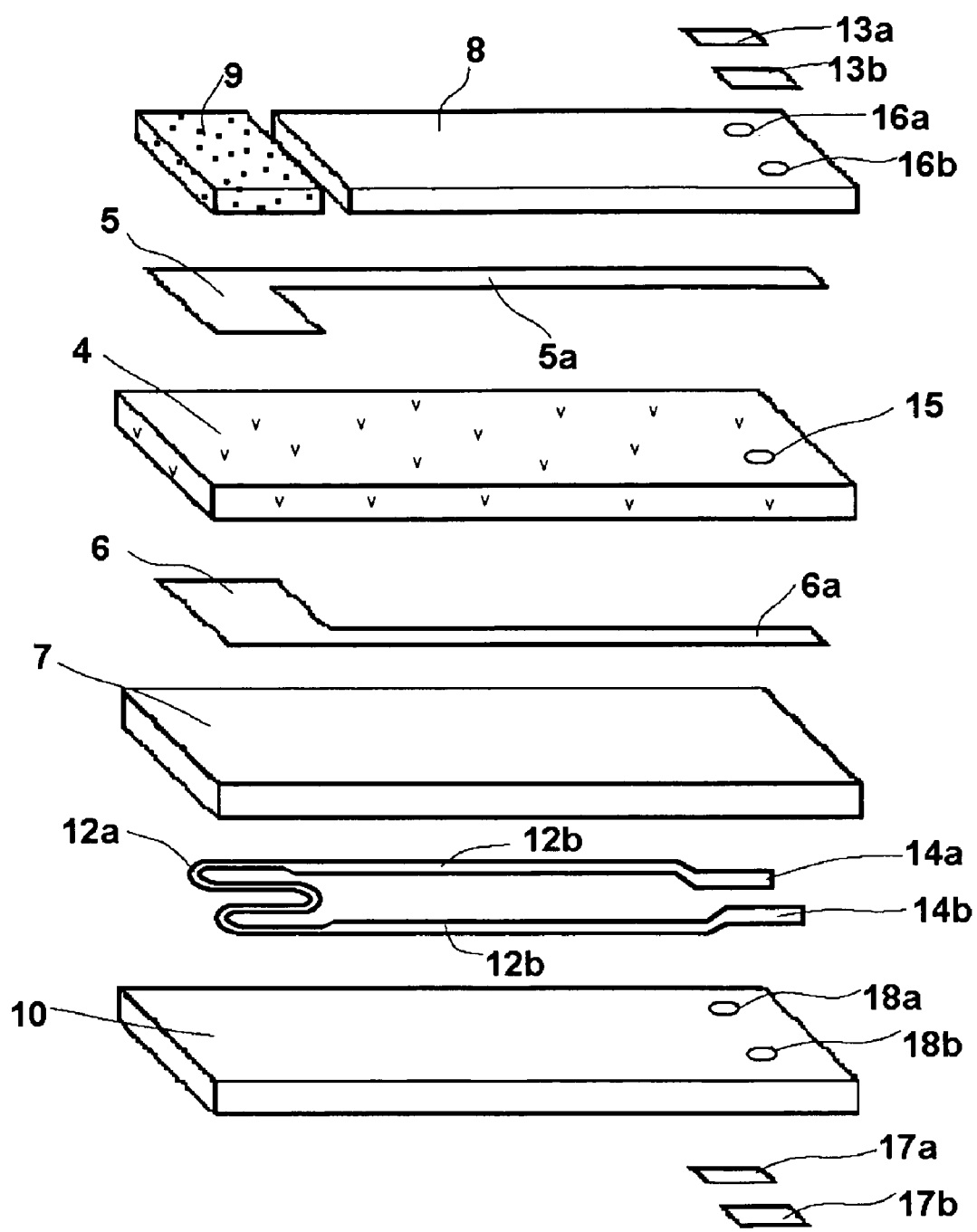
FIG. 4 is an exploded perspective view showing the internal structure of the prismatic multilayer gas sensor element of FIG. 1.

The first and second leads (5a, 6a) are respectively connected to a measuring electrode 5 and a reference electrodes 6 at the gas sensing portion 2 as shown in FIG. 4. These leads run longitudinally in the posterior lead portion so as to be respectively connected to terminal pads (13a, 13b) formed on the top surface of the first non-porous alumina layer 8 and located near the rear end of the prismatic gas sensor 1. The first lead (5a) is connected to the first terminal pad (13a) via a hole (16a) formed through the first alumina layer 8 and the second lead (6a) is connected to the second terminal (16b) via a hole 15 penetrating the solid electrolyte layer 4 and via a hole 16b formed through the first alumina layer 8, as shown in FIG. 4.

A heating resistor (12a) is sandwiched by non-porous alumina layers (7, 10) and is laminated close to the electrodes (5, 6) constituting a gas sensing portion 2 so as to heat and activate the gas sensing portion 2 to a temperature of 600° C. or higher to burn off carbon-like soot accumulating on the gas sensing portion 2. The leads (12b) of the heating resistor (12a) sandwiched by the alumina layers (7, 8) longitudinally extend to form terminal-connecting portions (14a, 14b) that are connected respectively to external terminal pads (17a, 17b) formed on a rear end portion of the alumina layer 10 and via holes (18a, 18b) formed therethrough. A preferable material for the heating resistor (12a) and for the leads 12b thereof is platinum.

Longitudinal lateral surfaces of the posterior lead portion 3 are coated with a third non-porous alumina layer, as shown in FIGS. 1 and 2, according to the invention. These longitudinal lateral surfaces correspond to cut-surfaces that are made by cutting a laminate comprised of the solid electrolyte layer 4 and the alumina layers (7, 8, 10) in the laminating direction, and are therefore substantially perpendicular to top and bottom planer surfaces of the prismatic multilayer gas sensor element 1.

The third non-porous alumina layer 11 coated on the longitudinal lateral surfaces of the prismatic gas sensor 1 is co-fired with the solid electrolyte layer 4 laminated at least with the first and second non-porous alumina layers (8, 7) at a temperature of 1350-1550° C. so as to provide firm bonding strength.

FIG. 3 is a schematic cross-sectional view of the gas sensing cell portion 2, as cross-sectioned along line B-B' line of FIG. 1. As shown in FIG. 3, the gas sensing portion 2 formed at a distal end portion of the prismatic multilayer gas sensor element 1 comprises a zirconia solid electrode layer 4; a gas-detecting or gas-sensing electrode 5 formed on a top planer surface of the solid zirconia solid electrolyte layer 4; and a reference electrode 6 formed on a bottom planer surface of the zirconia solid electrolyte layer 4. The bottom planer surface of the zirconia solid electrolyte layer 4 and the reference electrode 6 formed thereon are entirely covered by a non-porous alumina layer 7 laminated on the bottom surface thereof. A heating resistor 12a for heating the gas sensing cell portion 2 comprising the solid electrolyte 4 and the electrodes (5, 6) disposed thereon is formed on the bottom surface of the non-porous alumina layer 7 and covered by another non-porous alumina layer 10. A porous alumina layer 9 is formed on the gas-sensing electrode 5 and the solid zirconia solid electrolyte layer 4 that constitutes the gas-sensing cell portion 2 is designed to be heated to a temperature higher than 600° C. by the heating resistor 12a.

The electrodes (5, 6) sandwiching the zirconia solid electrolyte 4 and leads 5a and 6a connected thereto are preferably made of platinum. Especially, the reference electrode 6 and lead 6a connected thereto are made of porous platinum, so as to allow air as a reference gas to communicate with the reference electrode 6 through the lead 6a.

Since the temperature of the longitudinal lateral surfaces declines as the distance from the gas sensing portion 2 increases toward the rear end of the prismatic gas sensor element 2, and is not elevated beyond 600° C., the third non-porous alumina layer (11) coated at the longitudinal lateral surfaces of the posterior lead portion is subjected to carbon or carbon-like soot accumulating thereon.

In forming the third non-porous alumina layer 11 coated on the longitudinal lateral surfaces of the posterior lead portion 3 of the prismatic gas sensor element 2, a paste or slurry containing a water solvent, a fine alumina powder having an average particle size of 0.2-0.6 µm and having an alumina purity of more than 99%, preferably of more than 99.5%, is used. The reason for using such a fine alumina powder is to allow the powder to fill the fine holes of ragged lateral surfaces made by cutting a green laminate comprising the solid electrolyte layer and alumina layers. As a result, a thin and uniform non-porous alumina coating layer is co-fired with the lateral surfaces of the prismatic gas sensor element 1. The use of high-purity alumina particles effectively prevents migration of metallic ions contained in inorganic substances such as $MgO$ and $SiO_2$ other than alumina, contained in the non-porous alumina layer 11.

A non-porous alumina layer 11 having improved resistance against carbon filtrating therethrough and improved insulating resistance is attained by double coating the paste on the longitudinal lateral surfaces of the green posterior lead portion 3. In other words, when the non-porous alumina layer (11) has a multilayer structure including at least a joining layer (11a) joined with the lateral surface of the solid electrolyte layer (4) and a surface layer (11b) joined with the joining layer (11a), carbon filtration is more effectively prevented so that a higher insulating resistance between the solid electrolyte layer 4 and a sensor housing is attained, compared to a conventional single layer alumina coating having the same thickness. The joining layer is simply formed by coating a layer of the above paste having a thickness of 3-20 µm on the lateral surfaces of the green posterior lead portion 11 and drying at a temperature of higher than about 100° C. so as to remove water solvent from the paste. Then, another layer of what can be the same paste is coated on the dried paste layer, and this second paste layer is then dried at a temperature of higher than about 100° C. Additional plural (e.g., 3 or more) alumina coating layers can further improve resistance against carbon filtration and increase insulting resistance, providing that the total fired thickness remains the same (i.e., up to a total fired thickness of about 30 µm). This is because an alumina layer formed on an underlying alumina layer fills fine alumina particles into pores or voids formed in the thin underlying alumina layer, thus forming a multilayer structured alumina layer of high density and having a substantially "non-porous" characteristic against carbon-like soot.

FIG. 5 is a perspective view, showing another prismatic multilayer gas sensor element 200 comprising plural solid electrolyte layers (103, 107) according to the present invention.

The prismatic multilayer gas sensor element 200 comprises a gas-sensing cell or gas-measuring cell portion 401 and a posterior lead portion 402 adjoining the gas-sensing cell portion 401.

Figure 7:
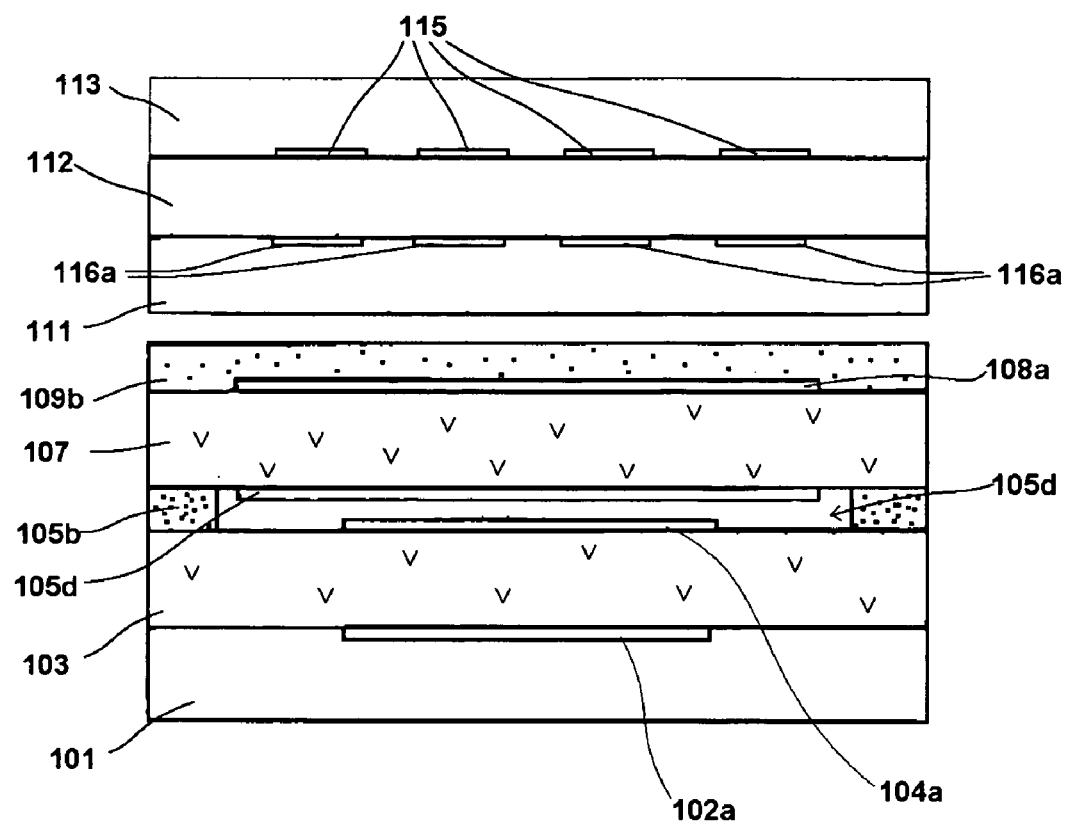
FIG. 7 is a schematic cross-sectional view, as cut along line D-D' line of FIG. 5, showing the internal structure of a gas-sensing portion of the prismatic multilayer gas sensor element of FIG. 5.

The gas-sensing cell portion 401 is formed at a distal end portion of the prismatic gas sensor element (200). The gas-sensing cell portion 401 comprises first and second zirconia solid electrode layers (103, 107) each having metallic electrodes (102a, 104a), (106c, 108a) formed thereon as shown in FIG. 7. The first zirconia solid electrolyte layer 103 constitutes an electromotive cell that detects a difference in oxygen partial pressure between a reference electrode (102a) and a gas-measuring electrode (104a). FIG. 7 is a schematic cross-sectional view along line D-D' line of FIG. 5, showing the internal structure of a gas-sensing cell portion 401 of the prismatic multilayer gas sensor element 200 of FIG. 5. The second zirconia solid electrolyte layer 107 shown in FIG. 7 constitutes a pumping cell that pumps oxygen into or out from chamber 105d formed between the gas measuring electrode (104a) and an inner pump electrode (106c) formed on the second zirconia solid electrolyte layer 107. Oxygen is pumped through the oxygen ion conductive zirconia solid electrolyte layer 107, an outer pump electrode (108a) formed on the second zirconia solid electrolyte layer 107 and a porous alumina layer (109b) covering the outer pump electrode (108a), to the outside of the prismatic gas sensor element 200. An exhaust gas exhausted, for example, from an internal combustion engine enters the chamber 105d through a porous alumina layer 105b that controls diffusion of the exhaust gas into the chamber 105d. By measuring the amount of oxygen that is pumped out or pumped into the chamber 105d, the oxygen content of the exhaust gas is thus detected by this two-cell type prismatic multilayer gas sensor element 200.

Figure 8:
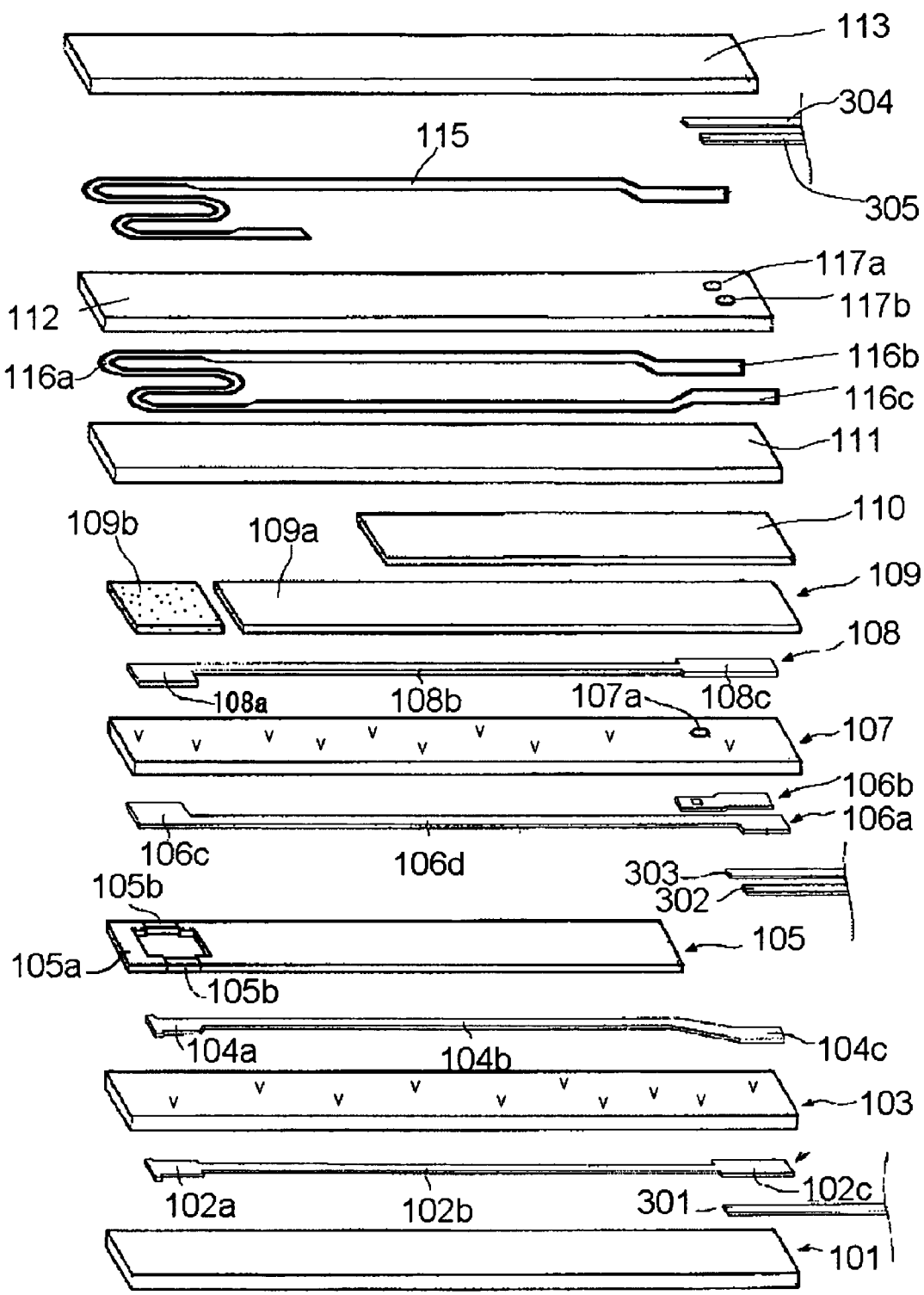
FIG. 8 is an exploded perspective view showing the internal structure of the prismatic multilayer gas sensor element of FIG. 5.

A ceramic heater comprising a heating resistor (116a) sandwiched by top and bottom alumina ceramic layers (112, 111) is placed close to the sensing cell portion 401 by cementing the bottom alumina layer 111 to non-porous alumina layer 109 by a cement layer 110, as shown in FIG. 7 and FIG. 8. A portion (109a) of the non-porous alumina layer 109, located close to the porous alumina layer 109b is not cemented with the bottom alumina layer 111 so as to maintain a gap between the ceramic heater and the porous alumina layer 109b. The top and bottom alumina layers 112 and 111 are made of an alumina ceramic containing about 97% by weight of $Al_2O_3$ and inorganic binders such as $MgO$, $SiO_2$ and $CaO$. The leads (116b, 116c) of the heating resistor are sandwiched by the non-porous alumina layers 111 and 112 and extend to a rear end portion of the posterior lead portion 402 so as to be connected to outer terminals (304, 305) by penetrating through holes (117a, 117b), respectively.

The posterior lead portion 402 adjoins the gas-sensing cell portion 401 and extends to a rear end portion of the prismatic gas sensor element 200 as shown in FIG. 5. The posterior lead portion 402 comprises the first and second zirconia solid electrolyte layers (103, 107) each extending from the gas-sensing cell portion 402 to the rear end portion of the prismatic gas sensor element 200, first top and bottom metallic leads (104b, 102b) sandwiching the extended first zirconia solid electrolyte layer 103, second top and bottom metallic leads (108b, 106d) sandwiching the extended second zirconia solid electrolyte layer 107, a first non-porous alumina layer (101) covering the bottom surface of the first solid electrolyte layer 103 and the first bottom lead 102b, an insulating alumina spacer 105 inserted between the first and second zirconia solid electrolyte layers (103, 107) and between the first bottom metallic lead (104b) and the second bottom metallic lead (106d), a second non-porous alumina layer 109a covering the top surface of the second solid electrolyte layer 107 and the top metallic lead (108b), and a third non-porous alumina layer (comprising layers 114a and 114b) co-fired with longitudinal lateral surfaces of the posterior lead portion 401, which lateral surfaces are substantially perpendicular to top and bottom planer surfaces of the prismatic multilayer gas sensor element 200.

The first top and bottom metallic leads (104b, 102b) connecting to the metallic electrodes (104a, 102a) and sandwiching the zirconia solid electrolyte layer 103 longitudinally extend to a rear end portion of the prismatic gas sensor 200, forming terminal pads (104c, 102c) on the top and bottom surface of the solid electrolyte layer 103, respectively, as shown in FIG. 8. The terminal pad (102c) is connected to an external lead 301 and the terminal pad (104c) is connected to an external lead 302.

The second top and bottom metallic leads (108b, 106d) sandwiching the extended second zirconia solid electrolyte layer 107 and connecting to the metallic electrodes (108a, 106c) are longitudinally extended to a rear end portion of the prismatic gas sensor 200, forming terminal pads (108c, 106a) on the top and bottom surface of the solid electrolyte layers 107, respectively. The terminal pad 106a is connected to the external lead 302. The terminal pad 108c is connected to another terminal pad (106b) formed on the bottom surface of the solid electrolyte layer 107 via a hole (107a) penetrating therethrough. The terminal pad (106b) is connected to an external lead 303.

The first non-porous alumina layer (101) is laminated with the solid electrolyte layer 103 so as to cover the bottom surface of the first solid electrolyte layer (103), the metallic electrode (102a) as a reference electrode and the first bottom lead (102b).

A second non-porous alumina layer 109 is laminated with the second solid electrolyte layer 107 so as to cover the top surface of the second solid electrolyte layer 107 and the top metallic lead (108b).

An insulating alumina spacer 105 inserted between the first and second zirconia solid electrolyte layers (103, 107) and between the first bottom metallic lead (104b) and the second bottom metallic lead (106d) is co-fired with the first and second zirconia solid electrolyte layers (103, 107) as shown in FIG. 5 and FIG. 8.

The temperature of the lateral surfaces of the posterior lead portion 401 of the prismatic multilayer gas sensor element 200 is not elevated to exceed 600° C. such that carbon-like soot accumulating thereon is not burned off. Therefore, the longitudinal laterals surfaces of the posterior lead portion 401 exposed to the exhaust gas are coated with a third non-porous alumina layer (114).

In order to prevent metallic ions such as Mg, Si and Ca ions from migrating from the inorganic binders of the alumina layers (111, 112) to the heating resistor (116a), an ion-migration preventing electrode 115 is connected to a ground, side lead (116b) of the heating resistor 116a. A protective insulating substrate 113 made of alumina ceramic is laminated with the insulating layer 112 so as to protect the ion-migration preventing electrode 115.

EXAMPLES

Next, examples of the prismatic multilayer gas sensor element comprising a zirconia solid electrolyte layer, embodied by the invention, will be explained. An evaluation test with respect to durability or resistance against "blackening" due to carbon fouling was conducted on the examples and comparative examples. These samples for evaluation relate to an oxygen sensor having a prismatic multilayer structure.

For producing the prismatic multilayer gas sensor elements for evaluation, a plural-cell type sensor having a multilayer structure comprising plural zirconia solid electrolyte layers as shown in FIG. 8 was adopted.

A green insulating ceramic layer 0.1-0.4 mm thick for producing the first and second non-porous alumina layers (101, 109) and for the insulating alumina spacer (105, 105a) may be prepared by a doctor-blade method from a slurry mixture formed by wet-blending an inorganic powder comprising 97% by weight of alumina powder and 3% by weight of silica and a plasticizer.

A green electrolyte ceramic layer about 0.4 mm thick for producing the zirconia solid electrolyte layers (103, 107) may be prepared by a doctor-blade method from a slurry mixture formed by wet-blending an inorganic powder comprising 97% by weight of zirconia and 3% by weight of alumina and a plasticizer. If another thin green electrolyte ceramic layer is needed between the first non-porous alumina layer 101 and the first solid electrolyte layer 103 so as to effectively protect the reference electrode 102a and the lead 102b in view of co-firing a laminate, a small amount of silica may be added for that purpose.

The slurry may be made by mixing 11 parts by weight of butyral resin and 5 parts of dibutyl phthalate (DBP) and 100 parts by weight of an inorganic powder.

A green metallic layer for the metallic electrodes (102a, 104a, 106c, 108a), the metallic leads (102b, 104b, 106d, 108b), and the metallic terminal pads (102c, 104c, 106a, 106b, 108c), to be formed on the zirconia solid electrolyte layer by screen printing, may comprise 90% by weight of platinum and 10% by weight of zirconia.

A porous alumina layer (105b) formed on the outer pump electrode (108a) of a pump cell and another porous alumina layer (105b) for gas diffusion control formed in a side entrance of a diffusion chamber (105d) may be made by screen printing a paste comprising, e.g., 83% by weight of alumina powder, 3% by weight of silica powder and 5-20% by weight of carbon powder.

After forming or printing the sensor constituents on each layer, the layers were laminated and bonded together to form a 150 mm square laminate by applying a pressure of 150 MPa thereto. Eight (8) pieces of green prismatic multilayer sensor elements were cut from the laminate.

On longitudinal lateral cut surfaces of the posterior lead portion 402, a slurry mixture formed by wet-blending an inorganic powder comprising 97% by weight of alumina powder and 3% by weight of silica with water was applied by screen printing.

Four kinds of samples were prepared for evaluation, by varying the number of alumina coating layers coated on the longitudinal lateral surfaces while maintaining a total thickness thereof to about 20 μm. Coating was done in a way that after one green layer is applied, the applied layer is dried by heating to a temperature of about 100° C., before applying the next coating. A first Example of the prismatic multilayer gas sensor element for the test was coated with two layers. A second Example was coated with four layers. A third Comparative Example was coated with a single layer, and a fourth Comparative Example was not coated.

Then, the green prismatic multilayer gas sensor samples were fired at a temperature of 1520° C. The length of an uncoated portion corresponding to the gas-sensing portion 401 in FIG. 5 was about 6.5 mm.

A ceramic heater comprising two alumina layers (111, 112) sandwiching a heating resistor (116a) and the leads (116b, 116c), having an ion migration preventing electrode 115 sandwiched by the alumina layer 112 and a protective alumina layer 113, was cemented with the top surface of the posterior lead portion 402 of each of the four samples to form a prismatic multilayer gas sensor element 200 as shown in FIG. 5.

Figure 9:
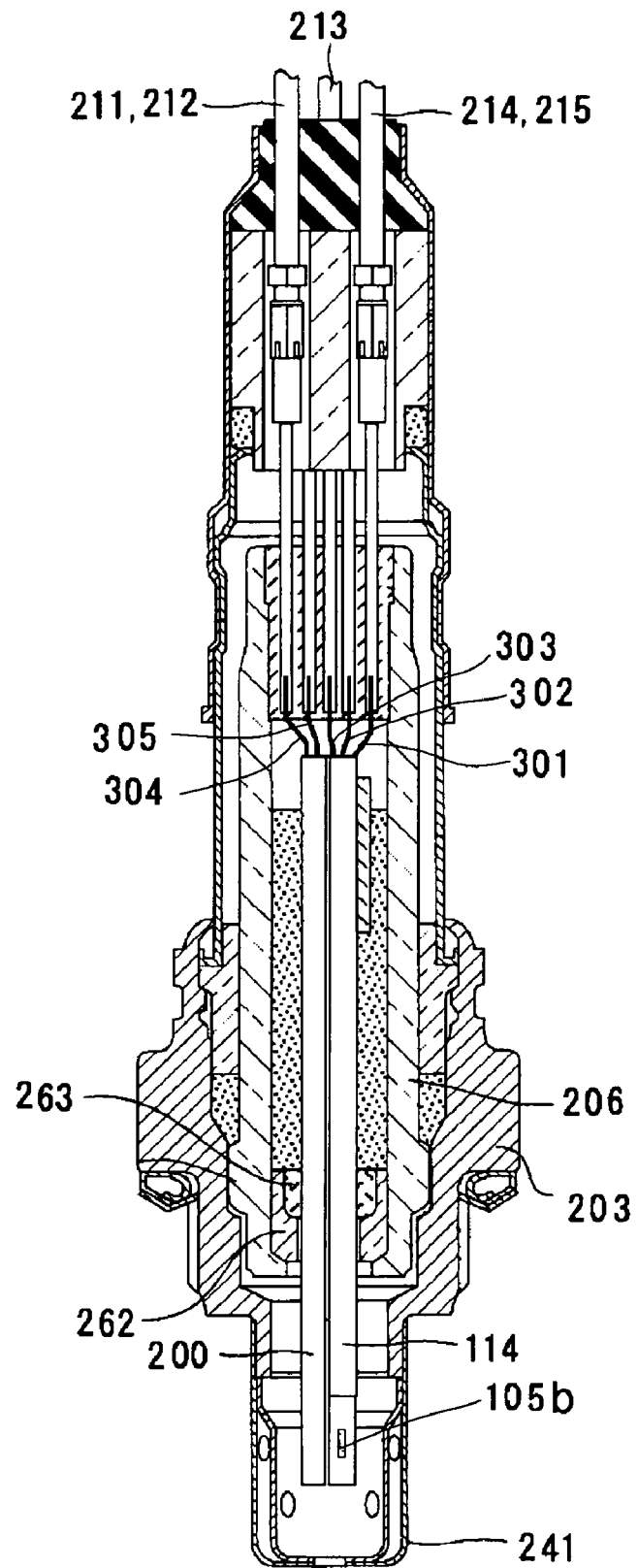
FIG. 9 is a sectional view showing the internal structure of a gas sensor including a prismatic multilayer gas sensor element of the present invention fixedly accommodated in a sensor housing.

Then, the four sample gas sensor elements were each incorporated in a sensor housing 203 as shown in FIG. 9 and subjected to evaluation for "blackening" of the zirconia solid electrolyte layers caused by carbon accumulation on the lateral surfaces of the prismatic gas sensor elements.

Figure 10:
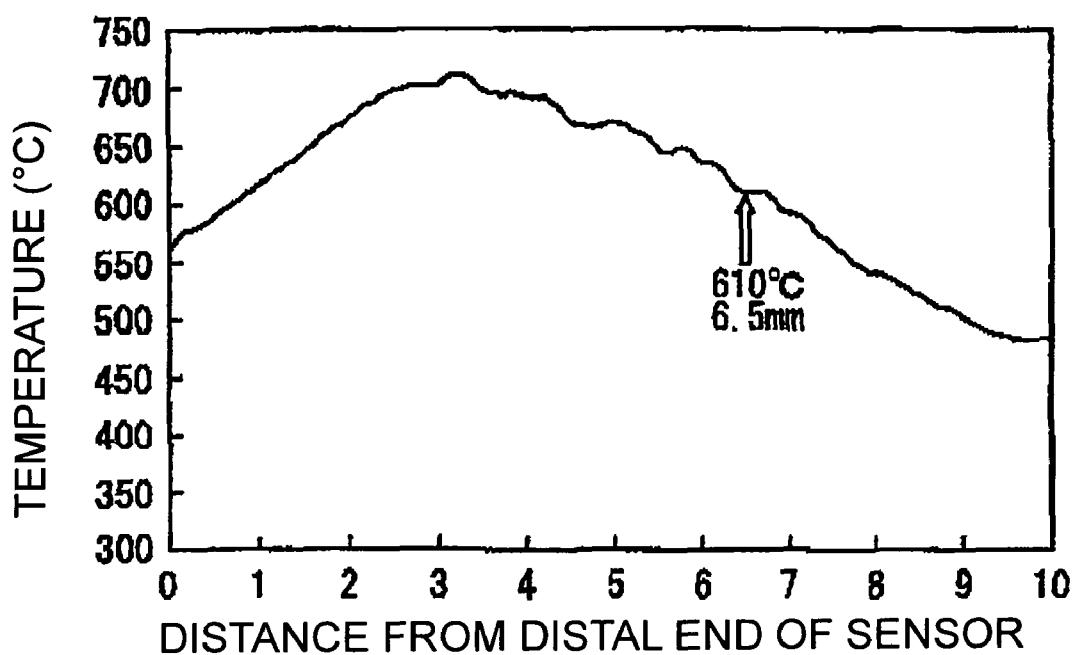
FIG. 10 is a graph showing temperature as a function of a distance from a distal end of the prismatic multilayer gas sensor element.

First, the temperature distribution as a function of distance from the distal end of the prismatic gas sensor element was measured, when incorporated in a typical sensor housing as shown in FIG. 9 operated as an A/F sensor with the ceramic heater heating the element. The temperature distribution of the prismatic multilayer gas sensor element in its longitudinal direction during actual use is shown in FIG. 10, which provides a thermo-positional relationship between the gas sensing cell portion and the posterior lead portion in view of effective thermal oxidation or burning off of carbon-like soot accumulating on the prismatic multilayer ceramic gas sensor element.

In order to facilitate evaluation of carbon-fouling causing "blackening" of the solid electrolyte layers, carbon was pre-sprayed on each sample gas sensor element incorporated in the sensor housing 203 and projecting inside a metallic protector 241 thereof, with the gas sensing portion masked by a masking tape, to the extent that the surface resistance across the alumina layer 114 of the posterior lead portion 402 and insulating members (206, 262, 263) supporting the sensor element 200 inside the metallic housing 203 was reduced to less than 1 k ohm. The resistance measured between the metallic housing 203 and each of external lead wires (211, 212) connected to the heater terminals (304, 305) and the resistance measured between the metallic housing 203 and each of the metallic leads (213, 214, 215) connected to the sensor terminals (303, 302, 301) were all more than 1 M ohm.

After unmasking the gas sensing portions, the gas sensors each incorporating the sample sensor element were operated for 14 hours in a fuel-rich atmosphere with A/F=11.5 and at a temperature of 450° C.

After this operating test, the resistances as mentioned above were measured. The resistance measured between the metallic housing 203 and each of the external lead wires (211, 212) connected to the heater terminals (304, 305) were more than 1 M ohm. The resistance measured between the metallic housing 203 and each of the metallic leads (213, 214, 215) connected to the sensor terminals (303, 302, 301) of the first and second Example sensor elements were all more than more than 1M ohm. However, the resistance measured between the metallic housing 203 and each of the metallic leads (213, 214, 215) connected to the sensor terminals (303, 302, 301) of the third and fourth Comparative Examples were less than 500K ohm and less than 300K ohm, respectively.

Then, carbon adhered to the surfaces of the sample gas sensor elements 200 was eliminated by ultrasonic cleaning. Then, the lateral surfaces of the Example elements were examined using a metallographic microscope to see if blackening or deoxidization of the solid electrolyte layers had occurred.

The first and second Example sensor elements according to the invention did not show any blackening. However, the third and fourth Comparative Example sensor elements showed prominent blackening of the solid electrolyte layers. The "blackened" state of the zirconia solid electrolyte layers of the fourth Comparative Example sensor element was almost pitch-dark and much darker than the third Comparative Example sensor. The examined surfaces of the third and fourth Example sensors indicated that "blackening" had started from small black spots and then had spread therefrom.

The first and second Example sensor elements according to the invention have advantageously improved in resistance against carbon soot-fouling or deoxidization of the zirconia solid electrolyte layer, and improved a thermo-positional relationship between the gas sensing cell portion and the posterior lead portion in view of effective thermal oxidation or burning off of carbon-like soot accumulating on the prismatic multilayer ceramic gas sensor element.

It should further be apparent to those skilled in the art that various changes in form and detail of the invention as shown and described above may be made. It is intended that such changes be included within the spirit and scope of the claims appended hereto.

This application is based on Japanese Patent Application No. 2005-32241 filed Feb. 8, 2005, the disclosure of which is incorporated herein by reference in its entirety.

What is claimed is:

1. A prismatic multilayer gas sensor element having a substantially rectangular cross section, comprising:
   a gas-sensing cell portion disposed at a distal end portion of the prismatic gas sensor element, comprising a zirconia solid electrolyte layer and a gas-detecting electrode and a reference electrode disposed on top and bottom planar surfaces of the zirconia solid electrolyte layer, respectively;
   a posterior lead portion adjoining to the gas-sensing cell portion and extending to a rear end portion of the prismatic gas sensor element, comprising the zirconia solid electrolyte layer longitudinally extending from the gas-sensing cell portion, a first metallic lead and a second metallic lead connected to the gas-detecting electrode and the reference electrode, respectively, the first and second metallic leads being disposed on the top and the bottom planar surfaces of the solid electrolyte layer and extending from the posterior lead portion, respectively, a first non-porous alumina layer covering the top planar surface of the zirconia solid electrolyte layer and the first metallic lead disposed thereon, and a second non-porous alumina layer covering the bottom planar surface of the zirconia solid electrolyte layer and the second metallic lead disposed thereon; and
   a heating resistor sandwiched by insulating layers and positioned in the vicinity of the gas-sensing cell portion so as to heat the gas-sensing cell portion to a temperature of more than 600° C.;
   wherein longitudinal lateral surfaces of the posterior lead portion, which longitudinal lateral surfaces are substantially perpendicular to top and bottom planar surfaces of the prismatic multilayer gas sensor element, and which longitudinal lateral surfaces are heated by the heating resistor to a temperature not exceeding 600° C., are coated with a third non-porous alumina layer,
   wherein the third non-porous alumina layer comprises a joining layer joined with a lateral surface of the solid electrolyte layer and a surface layer joined with the joining layer, and
   wherein the third non-porous alumina layer is non-porous against carbon intrusion such that carbon particles are prevented from passing through the third non-porous alumina layer and reaching the solid electrolyte layer.

2. The prismatic multilayer gas sensor as claimed in claim 1, wherein the gas-sensing cell portion is located within a distance of about 8 mm or less from the distal end of the prismatic multilayer gas sensor element.

3. The prismatic multilayer gas sensor as claimed in claim 1, wherein a lateral surface of the zirconia solid electrolyte layer constituting the gas-sensing cell portion is not coated with any non-porous alumina layer.

4. The prismatic multilayer gas sensor element as claimed in claim 1, wherein the third non-porous alumina layer is co-fired with the posterior lead portion and has a fired thickness of 2-30 µm.

5. A prismatic multilayer gas sensor element having substantially a rectangular cross section comprising:
a gas-sensing cell portion disposed at a distal end portion of the prismatic gas sensor element, the gas-sensing cell portion comprising first and second zirconia solid electrolyte layers each having metallic electrodes disposed thereon;
a posterior lead portion adjoining the gas-sensing cell portion and extending to a rear end portion of the prismatic gas sensor element, comprising first and second zirconia solid electrolyte layers each extending from the gas-sensing cell portion to a rear end portion of the prismatic gas sensor element, first top and bottom metallic leads sandwiching the extended first zirconia solid electrolyte layer, second top and bottom metallic leads sandwiching the extended second zirconia solid electrolyte layer, a first non-porous alumina layer covering the bottom surface of the first solid electrolyte layer and the first bottom lead, an insulating alumina spacer arranged between the first and second zirconia solid electrolyte layers and between the first bottom metallic lead and the second bottom metallic lead, and a second non-porous alumina layer covering the top surface of the second solid electrolyte layer and the top metallic lead; and
a heating resistor sandwiched by insulating layers and positioned in the vicinity of the metallic electrodes so as to heat the gas-sensing cell portion to a temperature of more than 600° C.;
wherein longitudinal lateral surfaces of the posterior lead portion, which longitudinal lateral surfaces are substantially perpendicular to top and bottom planar surfaces of the prismatic multilayer gas sensor element, and which longitudinal lateral surfaces are heated by the heating resistor to a temperature not exceeding 600° C., are coated with a third non-porous alumina layer,
wherein the third non-porous alumina layer comprises a joining layer joined with a lateral surface of the first solid electrolyte layer and joined with a lateral surface of the second solid electrolyte layer; and a surface layer joined with the joining layer, and
wherein the third non-porous alumina layer is non-porous against carbon intrusion such that carbon particles are prevented from passing through the third non-porous alumina layer and reaching the first solid electrolyte layer.

6. The prismatic multilayer gas sensor as claimed in claim 5, wherein the gas-sensing cell portion is located within a distance of about 8 mm or less from the distal end of the prismatic multilayer gas sensor element.

7. The prismatic multilayer gas sensor as claimed in claim 5, wherein a lateral surface of the zirconia solid electrolyte layer constituting the gas-sensing cell portion is not coated with any non-porous alumina layer.

8. The prismatic multilayer gas sensor element as claimed in claim 5, wherein the third non-porous alumina layer is co-fired with the posterior lead portion and has a fired thickness of 2-30 µm.

9. A method of manufacturing a multilayer prismatic gas sensor having a substantially rectangular cross section, which method comprises:
forming a plurality of unfired metallic electrodes on a top surface of a green zirconia solid electrolyte sheet;
forming a plurality of unfired metallic reference electrodes on the bottom surface of the green solid electrolyte sheet so as to obtain a plurality of gas sensing cells;
forming a plurality of unfired first and second metallic leads on the bottom and top surfaces of the green solid electrolyte layer, respectively, the first metallic leads connecting to the respective metallic reference electrodes and the second metallic leads connected to the respective metallic electrodes to form a plurality of posterior lead portions each adjoined to the respective plurality of the gas sensing cells;
forming an unfired laminate sheet by laminating a first green alumina sheet on the bottom surface of the green solid electrolyte layer and the first metallic leads and laminating a second green alumina sheet on the top surface of the green solid electrolyte layer and the second metallic leads;
cutting the unfired laminate sheet into a plurality of unfired prismatic multilayer gas sensor elements;
forming on cut-surfaces of the plurality of the posterior lead portions constituting unfired prismatic gas sensor elements, a first paste layer comprising alumina particles and a solvent and then drying the first paste layer to form a joining layer;
forming on the first dried paste layer, a second paste layer comprising alumina particles and a solvent and then drying the second paste layer to form a surface layer; and
firing the unfired prismatic multilayer gas sensor elements at a temperature of 1350-1550° C. so as to obtain plurality of fired prismatic gas sensor elements,
wherein an alumina layer comprising the joining layer and the surface layer is non-porous against carbon intrusion such that carbon particles are prevented from passing through the alumina layer and reaching the fired prismatic gas sensor elements.

10. The method as claimed in claim 9, wherein each of the first and second paste layers has an unfired thickness of about 3-25 µm, so that the alumina layer comprising the joining layer and the surface layer after firing has a total thickness of about 2-30 µm.

11. A gas sensor having a substantially rectangular cross section, the gas sensor comprising:
a gas-sensing portion disposed at a distal end portion of the gas sensor, the gas-sensing portion comprising an electrolyte layer and a gas-detecting electrode and a reference electrode disposed on top and bottom planar surfaces of the electrolyte layer, respectively;
a posterior lead portion adjoining to the gas-sensing portion and extending to a rear end portion of the gas sensor, the posterior lead portion comprising the electrolyte layer longitudinally extending from the gas-sensing cell portion towards the rear end portion, a first metallic lead and a second metallic lead connected to the gas-detecting electrode and the reference electrode, respectively, the first and the second metallic leads being disposed on the top and the bottom planar surfaces of the electrolyte layer and extending from the posterior lead portion towards the gas-sensing portion, respectively, a first alumina layer covering the top planar surface of the electrolyte layer and the first metallic lead disposed thereon, and a second alumina layer covering the bottom planar surface of the electrolyte layer and the second metallic lead disposed thereon; and a heating resistor sandwiched by the second alumina layer and an insulating layer and disposed in the gas-sensing portion;

wherein longitudinal lateral surfaces of the posterior lead portion, which longitudinal lateral surfaces are substantially perpendicular to top and bottom planar surfaces of the gas sensor, are coated with a third alumina layer, wherein the third alumina layer comprises a joining layer joined with a lateral surface of the electrolyte layer and a surface layer joined with the joining layer, and wherein the third alumina layer is non-porous against carbon intrusion such that carbon particles are prevented from passing through the third non-porous alumina layer and reaching the electrolyte layer.

12. The prismatic multilayer gas sensor element of claim 1, wherein the zirconia solid electrolyte layer, constituting the gas-sensing cell portion, comprises a tip end surface and two longitudinal lateral surfaces, and the two longitudinal lateral surfaces of the zirconia solid electrolyte layer are not coated with any non-porous alumina layer.

* * * * *